United States Patent [19]

Kalfas et al.

[11] Patent Number: 5,517,990
[45] Date of Patent: May 21, 1996

[54] STEREOTAXY WAND AND TOOL GUIDE

[75] Inventors: Iain H. Kalfas, Beachwood; Donald W. Kormos, Parma; David W. Piraino; Gene H. Barnett, both of Shaker Heights, all of Ohio

[73] Assignee: The Cleveland Clinic Foundation, Cleveland, Ohio

[21] Appl. No.: 224,955

[22] Filed: Apr. 8, 1994

Related U.S. Application Data

[63] Continuation-in-part of Ser. No. 983,390, Nov. 30, 1992, Pat. No. 5,309,913.

[51] Int. Cl.$^6$ .................................................. A61B 6/00
[52] U.S. Cl. ................................. 128/653.1; 128/653.4; 128/654; 606/130
[58] Field of Search ......................... 128/653.1, 653.2, 128/653.5, 653.4, 654; 606/130

[56] References Cited

U.S. PATENT DOCUMENTS

| | | | |
|---|---|---|---|
| 4,793,355 | 12/1988 | Crum et al. | 128/653 |
| 4,896,673 | 1/1990 | Rose et al. | 128/660.03 |
| 5,078,142 | 1/1992 | Siczek et al. | 128/653.1 |
| 5,230,338 | 7/1993 | Allen et al. | 128/653 |
| 5,257,998 | 11/1993 | Ota et al. | 606/130 |
| 5,279,309 | 1/1994 | Taylor et al. | 128/782 |
| 5,383,454 | 1/1995 | Bucholz | 128/653.1 |

FOREIGN PATENT DOCUMENTS

| | | |
|---|---|---|
| 427358A1 | 10/1990 | European Pat. Off. . |
| 456103A2 | 5/1991 | European Pat. Off. . |
| 469966A1 | 7/1991 | European Pat. Off. . |
| WO90/05494 | 5/1990 | WIPO . |
| WO91/04711 | 4/1991 | WIPO . |
| WO93/10710 | 6/1993 | WIPO . |
| WO94/06352 | 3/1994 | WIPO . |

OTHER PUBLICATIONS

"A Computer-Assisted System for 3-D Frameless Localization in Stereotaxic MRI" Clarysse, et al. IEEE Transactions on Medical Imaging, vol. 10, No. 4, Dec. 1991.
"A Frameless, Armless Navigational System for Computer-Assisted Neurosurgery", Kato, et al. J. Neurosurg 74:845-849, May, 1991.
"A Frameless Stereotaxic Operating Microscope For Neurosurgery" Friets, et al., IEEE Transactions on Biomedical Engineering, vol. 36, No. 6, Jun., 1989.
Cass Computer Assisted Stereotactic Surgery, MIDCO Medical Instrumentation and Diagnostics Corporation, advertising brochure, 1992.
"A Frameless Sterotaxic Operating Microscope for Neurosurgery", Friets, et al., IEEE Transactions on BioMedical Engineering, vol. 36, No. 6, Jun. 1989, pp. 608–617.

*Primary Examiner*—Ruth S. Smith
*Attorney, Agent, or Firm*—Fay, Sharpe, Beall, Fagan, Minnich & McKee

[57] ABSTRACT

A patient is secured to a subject support (10). A stereotaxic wand (40) is inserted into a tool guide (60). The wand has a tip portion (44), a portion extending along a pointing axis (46) of the wand, an offset portion (42) which is offset from the pointing axis of the wand, and at least two wand emitters (48, 50), mounted in alignment with the pointing axis of the wand. The two emitters selectively emit wand signals which are received by three receivers (14) mounted to a frame assembly (12). The tool guide includes a bore (66) extending along a guide axis. The bore is configured for selectively receiving a tool and the tip portion of the wand. An entry point and a trajectory are identified by the surgeon with the wand in the guide. More specifically, a trajectory and location of the wand are superimposed on a diagnostic image on a monitor (30). If the surgeon is satisfied with the entry point and trajectory shown on the monitor, a surgical tool is inserted into the bore while the tool guide is held along the designated trajectory and at the designated entry point.

23 Claims, 9 Drawing Sheets

5,517,990

STEREOTAXY WAND AND TOOL GUIDE

This application is a continuation-in-part of U.S. application Ser. No. 07/983,390, filed Nov. 30, 1992, now U.S. Pat. No. 5,309,913.

BACKGROUND OF THE INVENTION

The present invention relates to the medical diagnostic and surgical arts. It finds particular application in conjunction with neurosurgery and will be described with particular reference thereto. However, it is to be appreciated, that the invention will also find application in conjunction with neurobiopsy, CT-table needle body biopsy, breast biopsy, endoscopic procedures, orthopedic surgery, other invasive medical procedures, industrial quality control procedures, and the like.

A three-dimensional diagnostic image data of the brain, spinal cord, and other body portions is produced by CT scanners, magnetic resonance imagers, and other medical diagnostic equipment. These imaging modalities typically provide structural detail with a resolution of a millimeter or better.

Various frameless stereotactic procedures have been developed which take advantage of three-dimensional image data of the patient. These procedures include guided-needle biopsies, shunt placements, craniotomies for lesion or tumor resection, and the like. Another area of frameless stereotaxy procedure which requires extreme accuracy is spinal surgery, including screw fixation, fracture decompression, and spinal tumor removal.

In spinal screw fixation procedures, for example, surgeons or other medical personnel drill and tap a hole in spinal vertebra into which the screw is to be placed. The surgeon relies heavily on his own skill in placing and orienting the bit of the surgical drill prior to forming the hole in the vertebra. Success depends largely upon the surgeon's estimation of anatomical location and orientation in the operative field. This approach has led to suboptimal placement of screws that may injure nerves, blood vessels, or the spinal cord.

The present invention provides a new and improved technique which overcomes the above-referenced problems and others.

SUMMARY OF THE INVENTION

According to one aspect of the present application, a stereotaxic wand is provided. The wand has a tip portion, a portion extending along a pointing axis of the wand, an offset portion which is offset from the pointing axis of the wand, and at least two wand emitters mounted in a spaced relationship to the offset section in alignment with the pointing axis of the wand. In this manner, the tip portion and the wand emitters are colinear. The two wand emitters selectively emit wand signals which are received by at least three receivers positioned on a frame assembly. The frame assembly mounts the receivers in a fixed relationship to a subject support closely adjacent a means for securing a portion of the patient to the subject support. Reference emitters are mounted in a fixed known distance from the receivers. The reference emitters emit a reference signal which travels from the reference emitter the fixed distance to the receivers. A calibration means measures a reference travel time of the reference signal over the preselected distance. The calibration means generates a corresponding calibration factor. A wand position determining means determines a position of the wand tip portion by measuring wand signal travel times of the wand signals between the wand emitters and the three receivers mounted on the frame. The wand position determining means is connected with the calibration means to calibrate the wand signal travel times with the reference travel time. A tool guide defines a bore extending longitudinally therethrough along a guide axis. The bore is configured for selectively receiving either a tool or the tip portion of the wand.

According to another aspect of the present application, the tool guide includes a grooved portion defined along the guide axis. The groove is configured to receive the tool.

One advantage of the present application is that it facilitates more accurate surgical procedures.

Another advantage of the present invention is that it promotes patient safety.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1A:
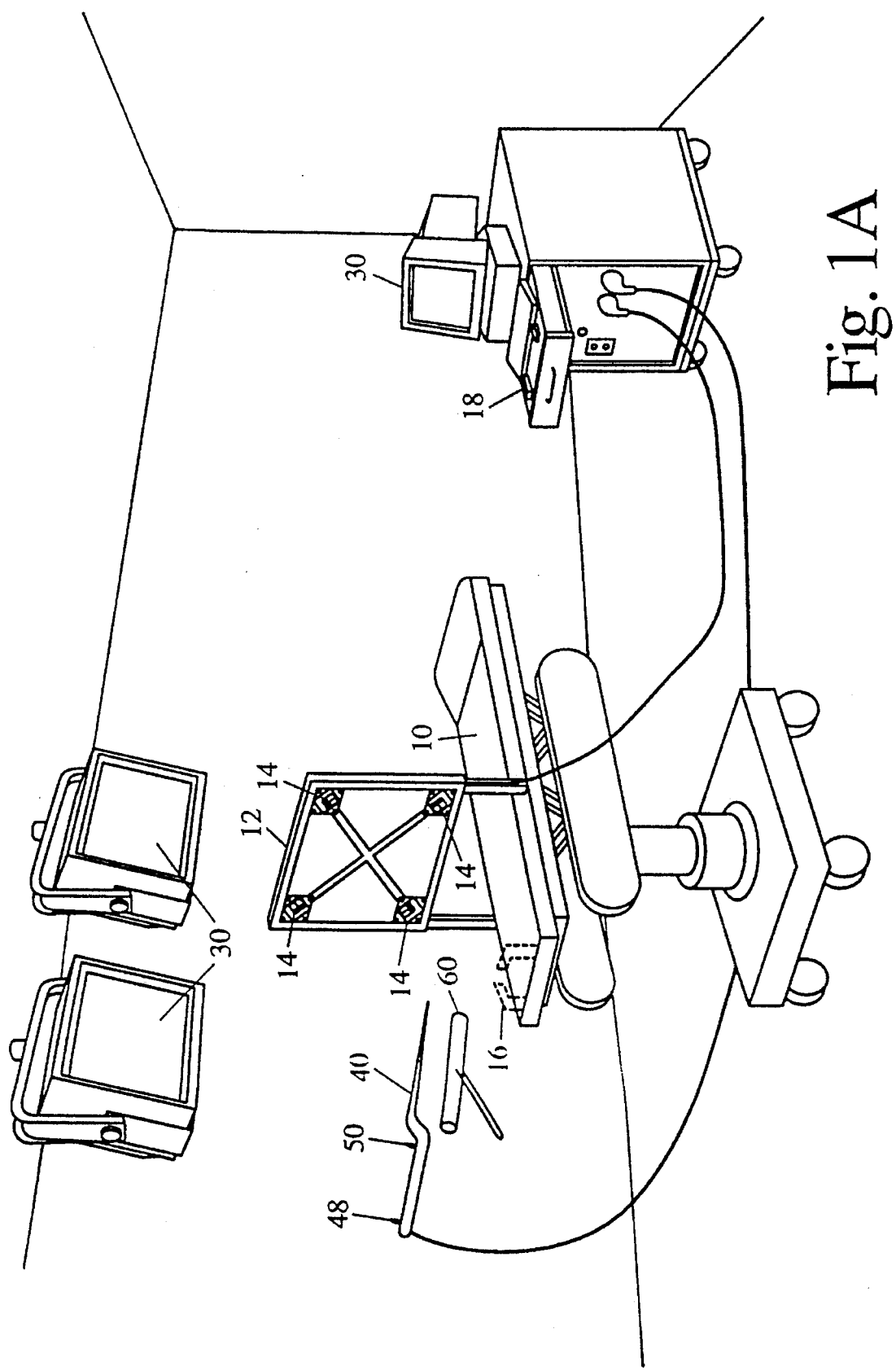
FIG. 1A is a perspective view of an operating room in which the present invention is deployed.

With reference to FIG. 1A, a subject, such as a human patient, is received on an operating table or other subject support 10 and appropriately positioned within the operating room. A frame 12 is mounted in a fixed relationship to the patient such that it is precisely positioned within the subject or subject support coordinate system. In the illustrated embodiment, the frame 12 is mounted to the patient support 10. Mounting the frame 12 to the patient support permits the patient support to be turned, raised, lowered, wheeled to another location, or the like, without altering the patient coordinate system. Alternately, the support may be mounted to a pole or other stationary support, the ceiling of the room, or the like. The frame 12 supports a plurality of receivers 14 such as microphones, radio frequency receivers, light sensitive diodes, other light sensitive receivers, and the like mounted at fixed, known locations thereon. A securing means such as a head clamp 16, securely positions a portion of the subject under consideration. The frame is mounted at a fixed or selectable angle from vertical such that the frame is positionable more toward the patient, yet still focusing on the region of interest of the patient.

Figure 1B:
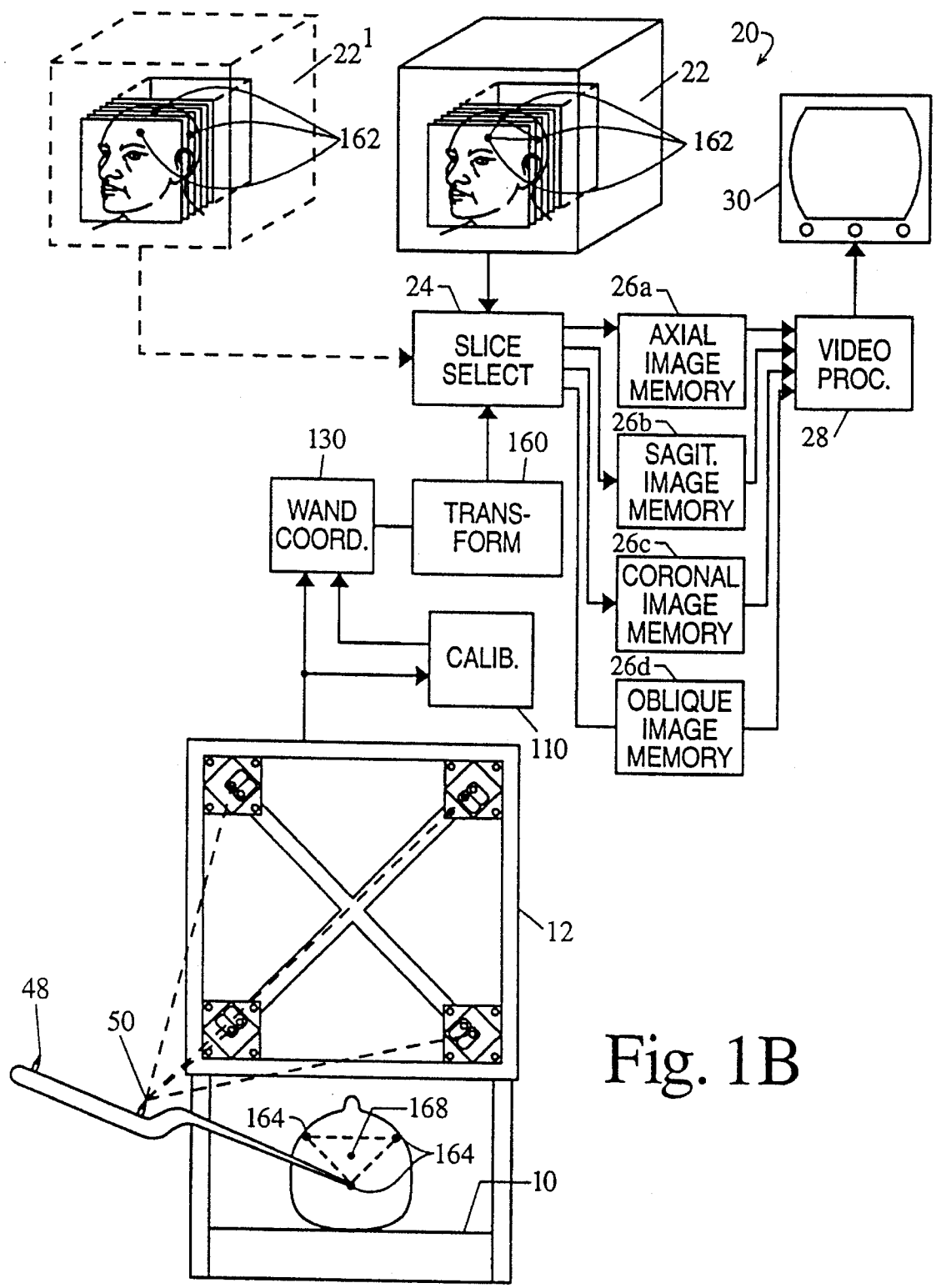
FIG. 1B is a block diagram of the image data manipulation of the system of FIG. 1A.

With continuing reference to FIG. 1A and further reference to FIG. 1B, an operator console 18 houses a computer system 20. Alternately, the computer system can be remotely located and connected with the control console 18 by cabling. The computer system includes a three-dimensional data memory 22. The stored three-dimensional image data preferably contains a video pixel value for each voxel or point in a three-dimensional rectangular grid of points, preferably a 256×256×256 grid. When each image value represents one millimeter cube, the image data represents about a 25.6 centimeter cube through the patient with one millimeter resolution. Because the data is in a three-dimensional rectangular grid, selectable orthogonal and other oblique planes of the data can readily be withdrawn from the three-dimensional memory using conventional technology. A plane or slice selector 24 selects various two-dimensional planes of pixel values from the three-dimensional memory for display.

The plane or slice selector selects at least three planes: axial, sagittal, coronal, and oblique planes through a selectable point of the patient. The pixel values which lie on the selected axial, sagittal, coronal, and oblique planes are copied into corresponding image memories 26a, 26b, 26c, and 26d. A video processor 28 converts the two-dimensional digital image representations from one or more of image memories 26 into appropriate signals for display on video monitors 30 or other appropriate image displays.

Figure 2A:
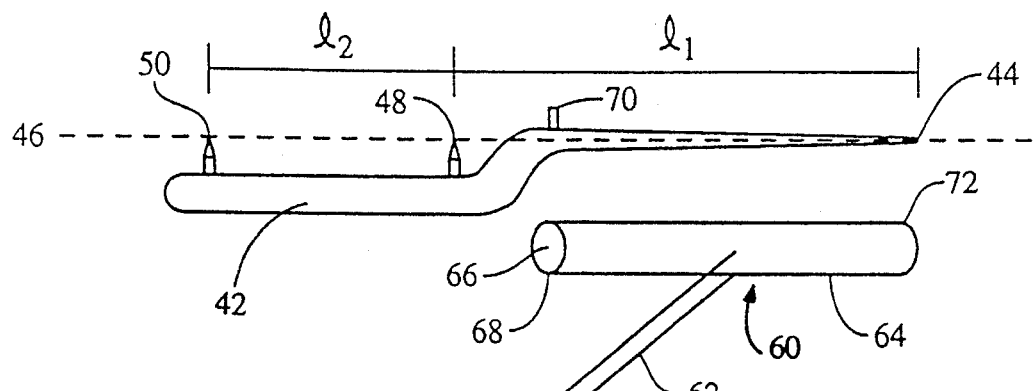
FIGS. 2A, 2B, 2C, 2D, 2E, 2F, and 2G illustrate alternate embodiments of the wand and guide.

With continuing reference to FIG. 1A and further reference to FIG. 2A, a wand 40, formed of suitable resilient material such as metal, has an offset 42 and a tip portion or proximal end 44. The offset 42 is connected to a portion extending along a pointing axis 46 of the wand. In this preferred embodiment, a pair of emitters 48 and 50 are mounted on the offset and disposed along the pointing axis 46 of the wand. The emitters, such as a spark emitter, radio frequency transmitter, infrared LED, or the like emit a signal that is received by the receivers 14. The first emitter 48 is a fixed known distance $\lambda_1$ from the tip 44 and the second emitter 50 is a fixed known distance $\lambda_2$ from the first emitter 48. The wand is readily sterilized by conventional techniques. Emitters 48 and 50 emit positioning signals used by a locator system to locate a coordinate and trajectory of the wand. The plane or slice selector 24 (FIG. 1B) selects patient image planes based on the coordinate and trajectory located. It is to be appreciated that more than two emitters may be mounted on the offset to provide additional positioning signals to be used by a locator system to locate the coordinate and trajectory of the wand.

The wand 40 is used in conjunction with a guide 60 to designate a coordinate and trajectory at which a surgical tool will be applied to the patient. The guide can be any guide or appliance which positions the wand 40 to establish a surgical trajectory. In the preferred embodiment, the guide 60 is a portable tool which has a handle 62 and a tube member 64 which defines an internal bore 66 to receive and accurately position the wand. The bore 66 of the tool guide has a diameter which allows for the non-simultaneous insertion of either the wand 40 or a surgical tool such as a drill, biopsy needle, and the like. Rather than being hand-held, the guide 60 can be mounted to other structures in the operating room, e.g. framed stereotaxic equipment. In intraoperative use, the wand 40 is inserted in the tool guide bore until the tip 44 aligns with a tool guide distal end 72. A wand stop 70 is positioned on the wand and abuts a proximal end surface 68 of the tool guide when the wand tip aligns with the proximal end 68. With the wand tip aligned with the tool guide end, the surgeon may commence probing the patient to seek an optimal coordinate and trajectory in which to insert the appropriate surgical tool. To this end, the surgeon maneuvers the wand and tool guide in combination to a proposed trajectory and actuates the emitters. Signals from the emitters are used in calculating the trajectory 46 and the end point 44 of the wand. The trajectory and end point are displayed on the monitor 30 superimposed on the three-dimensional image or selected image planes. The details of the process for correlating the coordinate system of the patient and the wand with the coordinate system of the image data is described below.

By viewing the display 30, the surgeon can identify the location of the wand tip with respect to anatomic structure, and the trajectory of the bore. If the trajectory is satisfactory, the wand is removed, the surgical tool is inserted, and the procedure is performed. If the trajectory is unsatisfactory, the wand is repositioned and its new trajectory determined and evaluated. This approach improves surgical planning when compared with prior approaches in which surgeons relied solely on their own estimation of the patient's anatomy. Following the identification of the appropriate trajectory and coordinate, the wand 40 is removed from the bore 66 of the guide 60 while the guide is held in position. Holding the guide 60 steady preserves the appropriate trajectory and position coordinates in the axial and sagittal planes determined by the wand. Thereafter, the appropriate surgical tool or appliance is inserted within the guide 60. With this approach, the surgical tool is properly positioned in the appropriate trajectory required to perform the surgical procedure.

The wand and tool guide are particularly useful in accurately identifying the optimal entry point, trajectory, and depth of insertion of screws to be placed into the patient's spinal column, as will be more fully described below.

Figure 2B:
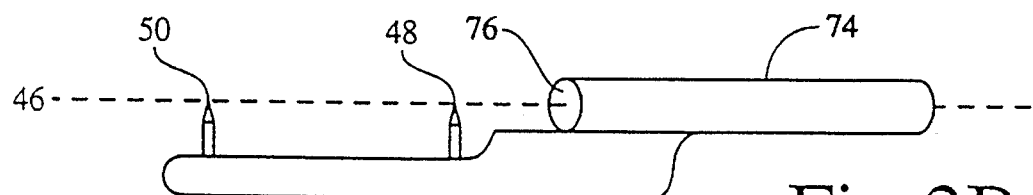
Figure 2C:
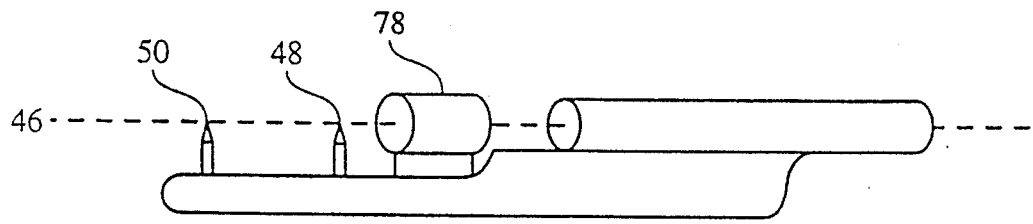
Figure 2D:
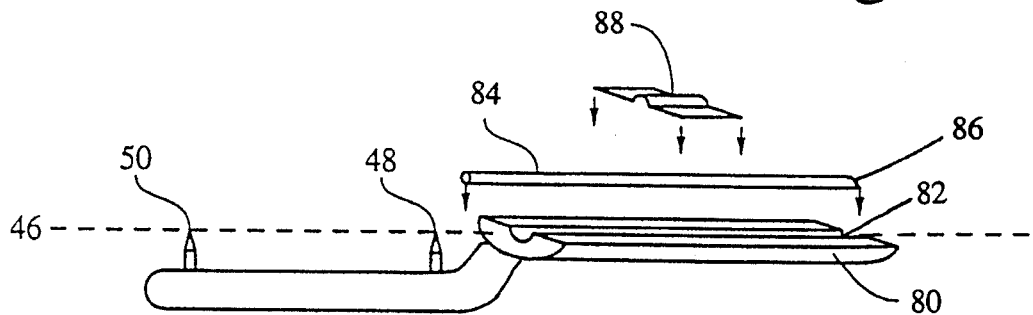

With reference to FIGS. 2B, 2C, and 2D alternative embodiments of the present invention are shown in which the guide is integrated into the wand. In general, each of the alternative embodiments contain a wand offset portion on which are mounted two or more emitters for emitting positioning signals. As in the preferred embodiment, emitters 48 and 50 are disposed along a pointing axis 46 of the wand. However, in the alternative embodiments, the central axis or pointing direction 46 aligns with a longitudinal axis of the guide means formed integrally with the wand. In each of the alternative embodiments, the guide means is connected to the wand offset portion via an extension.

With reference to FIG. 2B, a tubular portion 74 is integrated with the wand. The tubular portion defines a bore 76 extending along its longitudinal axis. In intraoperative use, the surgeon probes the patient with the proximal seeking to locate the proper coordinate and trajectory for the surgical tool. Once the coordinate and trajectory are located, the surgeon holds the offset portion while the surgical tool is inserted within the tube. Thereafter, the surgical tool is operated to perform the surgical procedure.

With reference to FIG. 2C, a second alterative embodiment is shown similar to the previously described alternative embodiment. However, in addition to the structure previously described, a laser 78 is mounted to the offset portion. Light emitting from the laser travels along the longitudinal pointing axis 46 of the bore 76 of the tubular member. In intraoperative use, the surgeon maneuvers the integrated wand and laser while viewing images displayed on the monitor 30. The images selected for display are based upon the coordinate and trajectory of the bore center point at the proximal end of the integrated wand. Once a proper coordinate and trajectory are identified, the integrated wand is held in place while the surgeon activates the laser. Light emitting from the laser intersects the bore center point at the proximal end.

With reference to FIG. 2D, a third embodiment is shown in which a grooved member 80 is incorporated into the wand. The grooved guide member portion is connected to the offset portion. The grooved member contains a groove 82 having a longitudinal axis which is in line with pointing axis 46 of the wand. This alternative embodiment finds particular usefulness in conjunction with needle biopsies. In intraoperative use, a biopsy needle 84 is positioned within the groove so that a tip 86 of the biopsy needle aligns with the groove center point at the proximal end of the integrated wand. The biopsy needle is held in place by a restraining means such as Velcro® straps 88 attached to the sides of the grooved member.

Figure 2E:
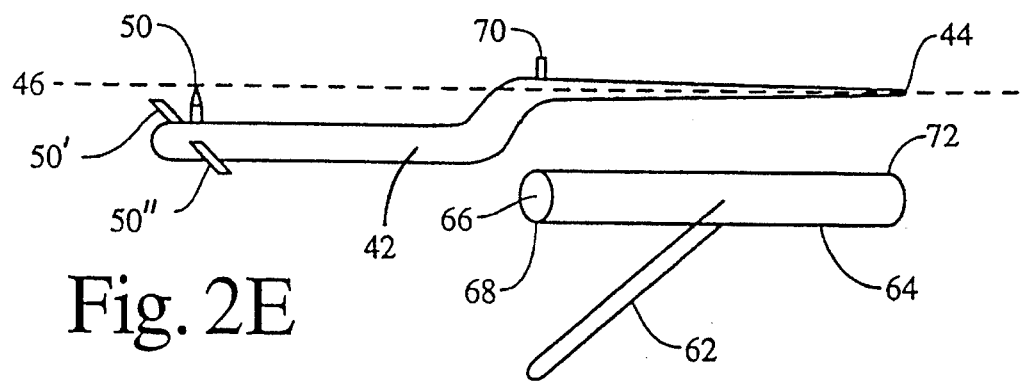

In the embodiment of FIG. 2E, the wand has emitters 50, 50', 50" mounted off the axis 46. Because the relationship between the emitter location and the axis 46 is fixed, once the emitters are located, the axis 46 is determined.

Figure 2F:
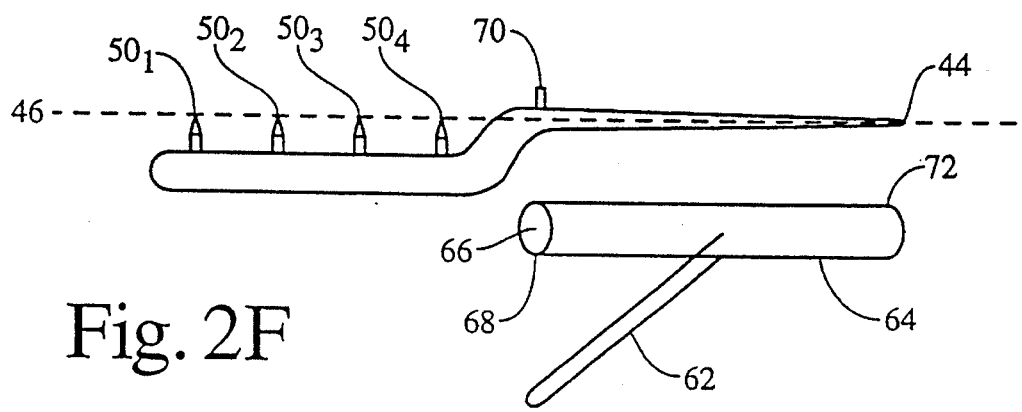

In the embodiment of FIG. 2F, there are more than two emitters $50_1, 50_2, 50_3, \ldots$. Although any two emitters would determine the axis 46, greater accuracy is obtained by redundantly determining the axis 46 and averaging the results. Preferably, a least squares fit is used to compensate for any deviation in the axis 46 determined by the various emitter pairs.

Figure 2G:
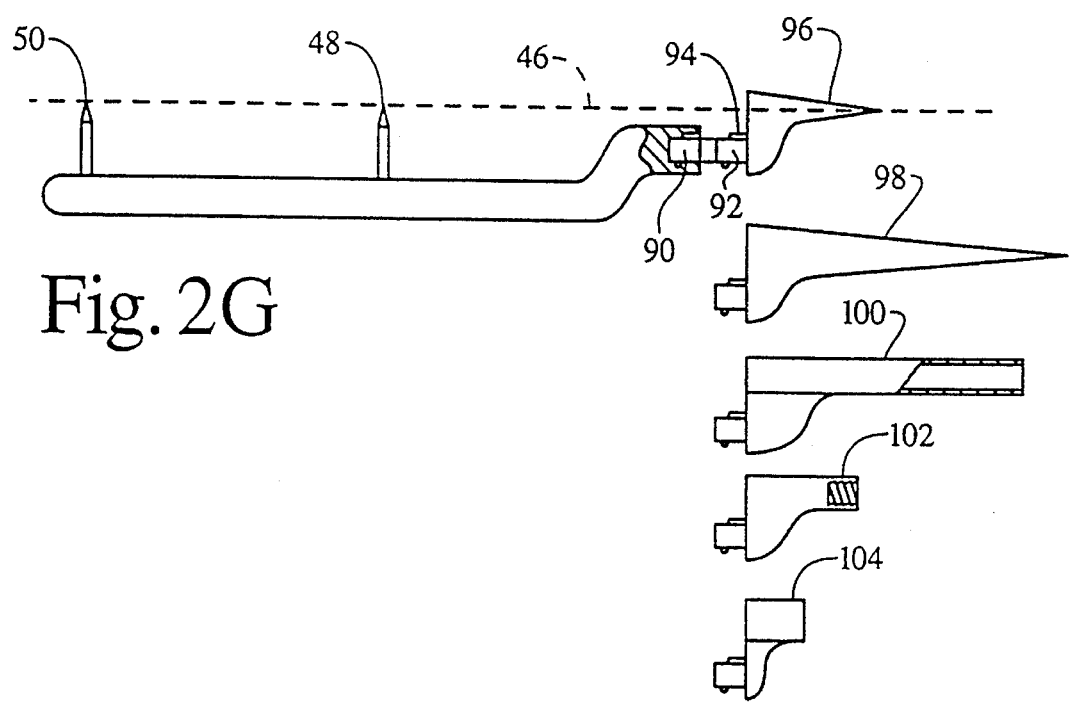

In the embodiment of FIG. 2G, the wand has interchangeable tips. The wand includes a first connector portion 90 which selectively connects with a second connector portion 92 of the tips. Various connector systems are contemplated such as a threaded bore and threaded shaft, a snap lock connector means, bayonet connector, spring lock, or other connector systems. A key and keyway system 94 or other means for fixing the alignment of the tips and the wand is particularly advantageous when the connector is off the axis 46.

Various tips are contemplated. A short tip 96 is provided for accurate registration. A longer tip 98 facilitates reaching deeper into interior regions of the subject. Tubular drill guides 100 can be provided in various diameters to accommodate different size drills. An adapter 102 enables endoscopes and other tools to be attached to the wand. Tools and equipment, such as an array of ultrasonic transducers 104, can be connected to the adaptor 102 or configured for direct connection to the wand. A wide variety of other tips for various applications are also contemplated.

The preferred embodiment uses the stereotaxic wand 40 to align the coordinate system of the operating room including the patient, the tool guide, and wand with the coordinate system of a previously prepared three-dimensional image stored in memory. Prior to identifying the proper coordinate and trajectory of the tool guide, the patient space is aligned with or referenced to the stored three-dimensional image data preferably using the following technique.

Figure 3:
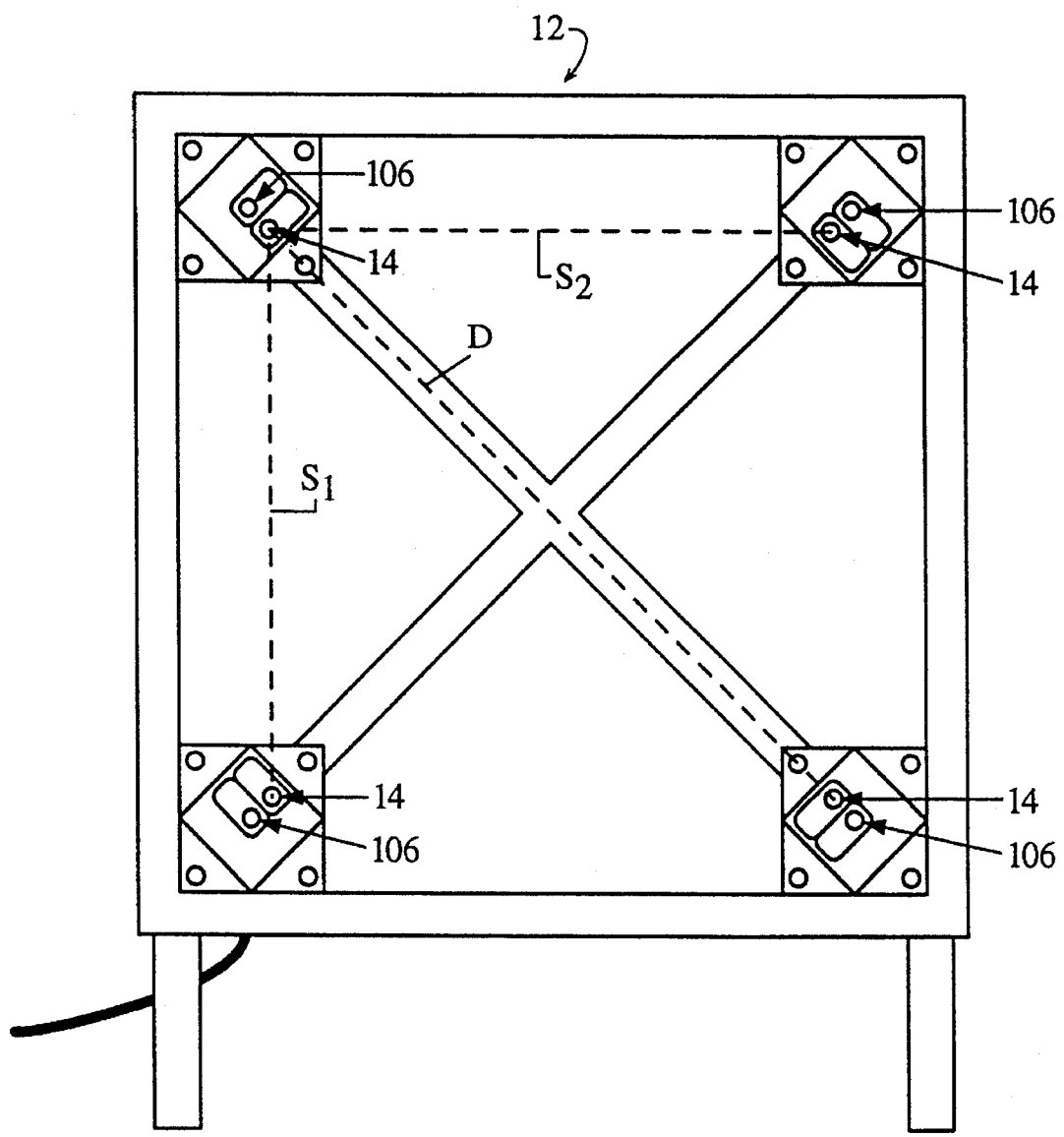
FIG. 3 is a detailed illustration of the locator assembly of FIG. 1.

With reference to FIG. 3, when the receivers 14 are microphones, a plurality of reference emitters 106 are mounted on the frame 12. The reference emitters are each spaced along side edges of the frame by known distances from adjacent receivers or microphones 14, e.g. by distances $S_1$ and $S_2$. Preferably $S_1=S_2=S$. Each reference emitter is also spaced by a distance D across the frame from an oppositely disposed reference emitter.

Figure 4:
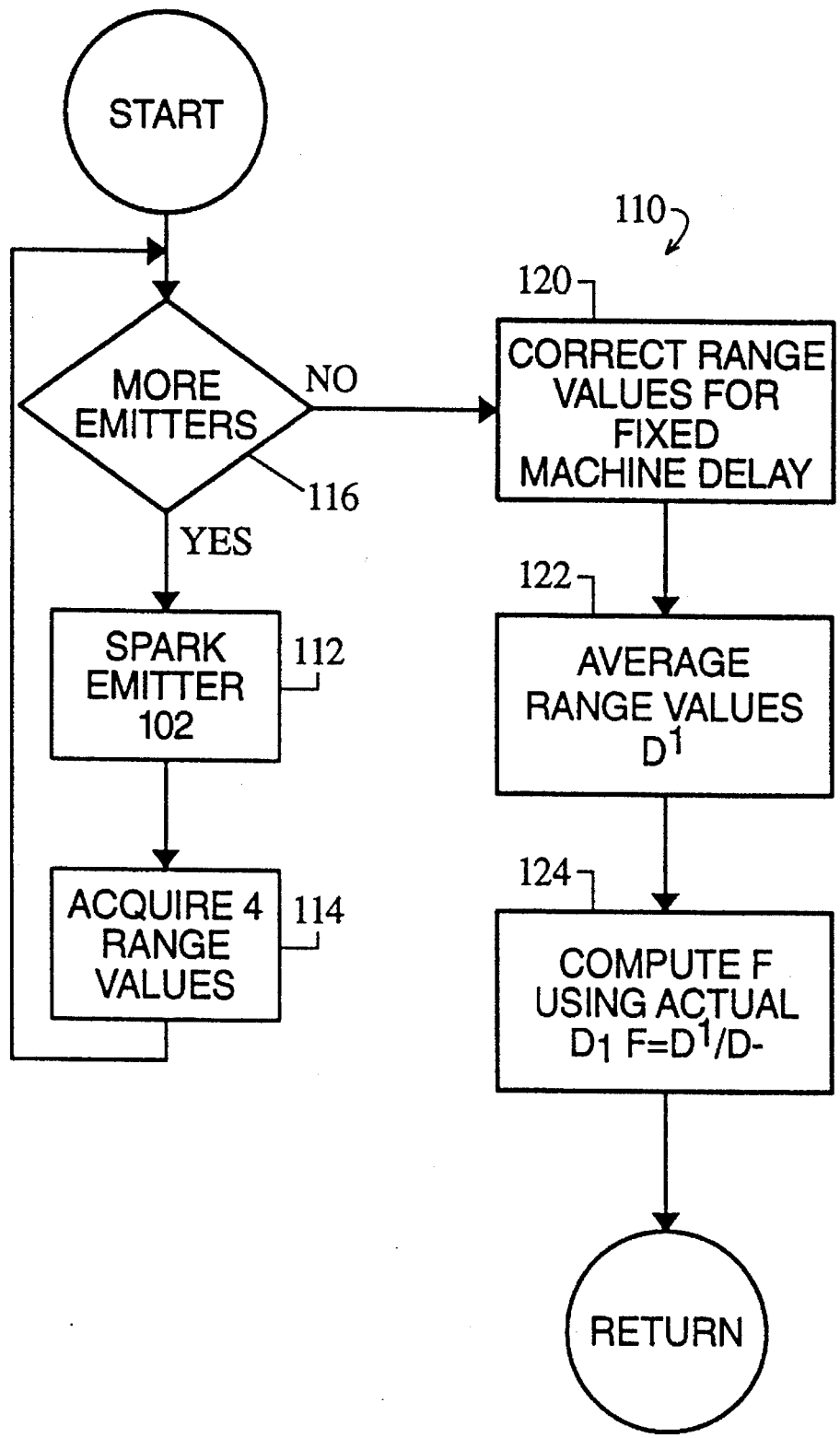
FIG. 4 is a diagrammatic illustration of one embodiment of calibration procedure in accordance with the present invention.

The distance from the wand emitters to the frame, hence the position of the wand relative to the patient, is determined by the travel time of the sound. The velocity of the sound pulse through air is dependent upon both the temperature, the humidity, and the chemical composition of the air. These factors can and do vary significantly during an operation and from procedure to procedure. As shown in FIG. 4, a calculation is performed to determine the speed of sound in the operating room. A calibration procedure 110 selectively pulses the reference emitters 106, receives the signals at microphone receivers 14, and processes the elapsed time information in accordance with the procedure of FIG. 4. More specifically, the calibration procedure 110 includes a step 112 for causing a first of the reference emitters 106 to emit a signal pulse. A step 114 acquires the range values D', i.e. the time required for the ultrasonic pulses to traverse the distance D. A step 116 causes this procedure to be repeated a preselected number of times, such as once for each of the four emitters illustrated in FIG. 3.

Once the travel time between each emitter and receiver pair has been obtained a preselected number of times, a step 120 corrects the times for fixed machine delays. That is, there is a fixed, small delay between the time when the command is given to fire the reference emitters 106 and the time that they actually produce a detectable ultrasonic signal. Analogously, there is a small delay between the time that the ultrasonic pulses reach the receiver or microphone 14 and the time that it becomes a measurable electrical signal received by the computer processor. These delays are subtracted from the times measured by step or step 114. An averaging means 122 averages the actual times after correction for the machine delays for transmission of the ultrasonic pulse between the transmitter and receiver. The time over the range values D' provide the most accurate results. A step 124 computes a calibration factor F indicative of the current speed of the ultrasound signal adjacent the patient in the operating room. In the preferred embodiment, the calibration factor F is a ratio of the sonicly measured distance D' versus a precise mechanical measurement of the distance D.

Figure 5B:
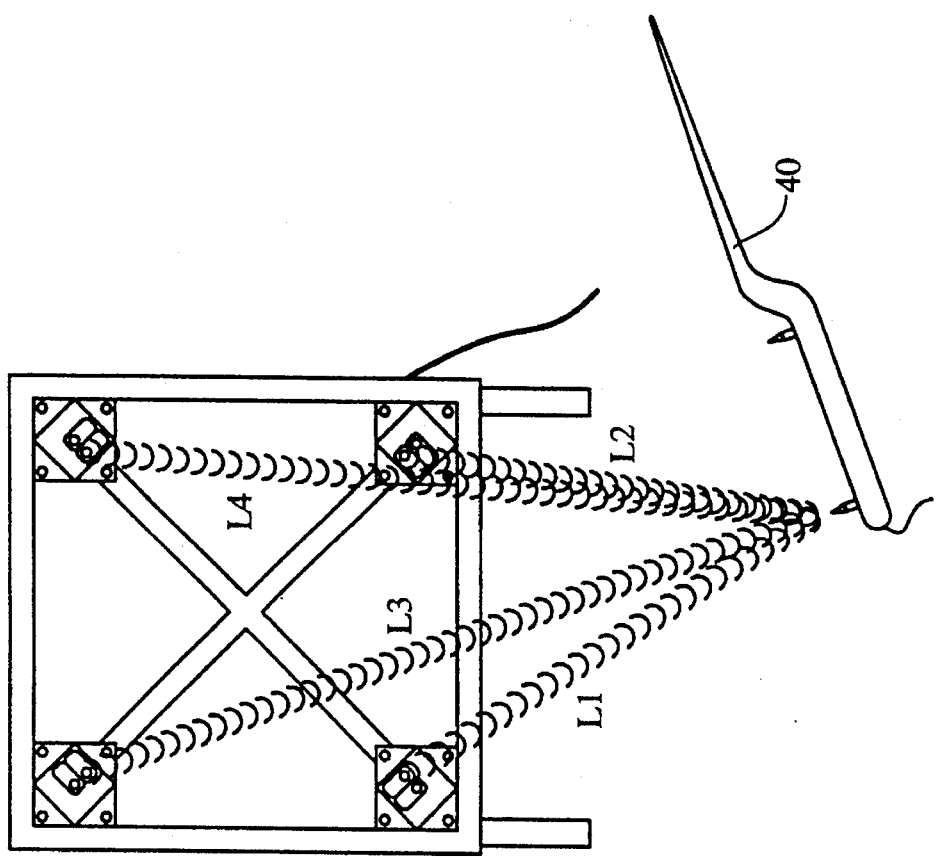
FIGS. 5A and 5B are diagrammatic illustrations of the wand and locator relationship.
Figure 5A:
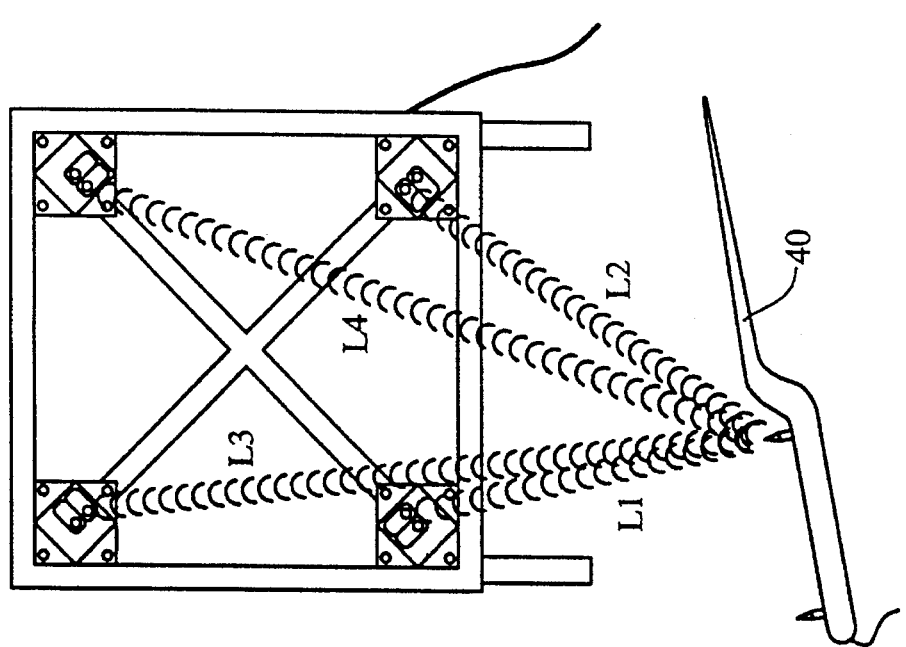
Figure 5C:
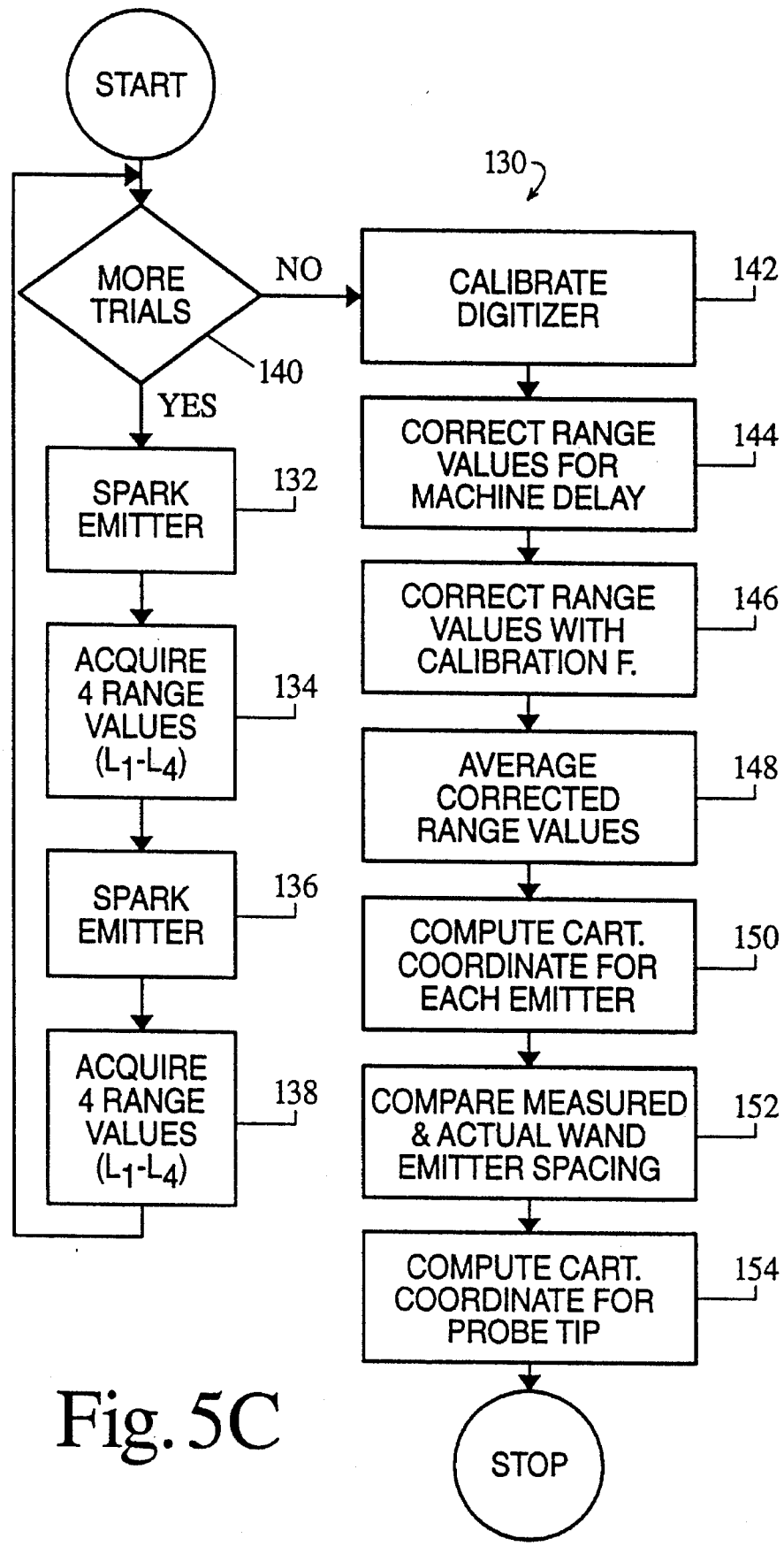
FIG. 5C is a flow diagram of the wand location procedure.

With reference to FIGS. 5A, 5B, and 5C, a wand coordinate and trajectory determining procedure 130 determines the position of the two emitters 48 and 50, respectively. More specifically, a step 132 causes the emitter 48 to emit an ultrasonic signal. The receivers 14 on the frame 12 receive the ultrasonic signal at corresponding times $L_1$–$L_4$. A step 134 acquires and retains these times. A step 136 causes the second emitter 50 to transmit. A step 138 acquires the four times $L_1$–$L_4$ which are required for the ultrasonic signals to pass from the second emitter to the microphones 14. The speed of ultrasonic transmission and accuracy of transmission times are such that these distances can be measured to within a millimeter or better. A step 140 causes the emitters to emit and corresponding data values $L_1$–$L_4$ to be acquired each of a plurality of times to improve digitation accuracy, e.g. two times.

When sonic emitters are used, a step 142 causes the calibration means 110 to perform the steps described in conjunction with FIG. 4 in order to provide a current indication of the velocity of sound adjacent to the patient. Of course, the calibration procedure of FIG. 4 may be performed immediately before steps 132–138 or intermittently during the collection of several data values for averaging. A step 144 corrects the values $L_1$–$L_4$ for the fixed machine delay discussed above in conjunction with step 120. A step 146 corrects each of the times $L_1$–$L_4$ that were required for the ultrasonic signals to travel from the first and second emitters 48, 50 to the receivers 14 in accordance with the correction factor F determined by step 124. An averaging means 148 averages the delay and calibration corrected times $L_1$–$L_4$, hence distances between each of the wand emitters 48, 50 and each of the receivers 14. From these distances, provided at least three receivers 14 are provided, a step 150 calculates the Cartesian coordinates $(x_1, y_1, z_1)$ and $(x_2, y_2, z_2)$ in the patient space for the two emitters 48 and 50. The first emitter coordinates $x_1, y_1, z_1$ are calculated from three of the four range values $L_1$–$L_4$. With $L_4$ disregarded, the coordinates are calculated as follows:

$$x_1 = [(L_1^2 - L_2^2) + S^2]/2S \quad (1a),$$

$$y_1 = [(L_1^2 - L_3^2) + S^2]/2S \quad (1b),$$

$$z_1 = [(L_1^2 - x_1^2 - y_1^2)]^{1/2} \quad (1c),$$

where $S = S_1 = S_2$ as defined in FIG. 3. Preferably, the three selected range values are the three shortest of $L_1$–$L_4$. Similar computations are calculated for $x_2$, $y_2$, and $z_2$ coordinates of the second emitter. A step or means 152 checks the validity of the measurement. More specifically, the known separation between the wand emitters is compared with the separation between the measured coordinates $x_1, y_1, z_1$ and $x_2, y_2, z_2$ of the wand emitters, i.e.:

$$|Sep_{known} - [(x_1 - x_2)^2 + (y_1 - y_2)^2 + (z_1 - z_2)^2]^{1/2}| \leq error. \quad (2)$$

If the measured and known separation is greater than the acceptable error, e.g. 0.75 mm when measuring with a resolution of 1 mm, an erroneous measurement signal is given. The measurement is discarded and the surgeon or other user is flagged to perform the measurement process 130 again. From the coordinates of the two emitters 48, 50, and from the geometry of the wand discussed in FIG. 2, calculates a step 154 the Cartesian coordinates $(x_0, y_0, z_0)$ for the wand tip 44.

The tip coordinates $x_0$, $y_0$, $z_0$ are defined by:

$$r = \lambda_1/\lambda_2 \quad (3a),$$

$$x_0 = (1+r)x_1 - rx_2 \quad (3b),$$

$$y_0 = (1+r)y_1 - ry_2 \quad (3c),$$

$$z_0 = (1+r)z_1 - rz_2 \quad (3d).$$

Before the wand and tool guide can be used to locate a proper coordinate and trajectory for a surgical tool such as a drill, the patient space $(x,y,z)$ is aligned with the image space $(x',y',z')$ stored in memory. Aligning the spaces begins with referencing known positions or points 164 in the patient space with the wand tip. For example, the tip 44 of the wand may be referenced to three independent positions of the vertebra, i.e. the tips of the spinous and traverse processes. These positions 164 on the vertebra are compared with the relative position of pixels 162 in the image space. Thereafter, with reference to FIG. 6, a transform 160, as shown in FIG. 6, transforms the coordinates of the patient space into the coordinate system of the image space. Fiducials can also be used by the transform 160 to transform or match the coordinates of other patient space points 164 into the coordinate system of the image space. To this end, three or more fiducials or markers are affixed at three or more spaced points on the patient's body. The fiducials are visible in the imaging medium selected such that they show up as readily identifiable dots 162 in the resultant image data. The fiducials are markers or small beads that are injected with radiation opaque and magnetic resonance excitable materials. A small dot or tattoo is made on the patient's skin and a fiducial is glued to each dot. This enables the position 164 of the fiducials to be denoted even if the fiducials are removed in the interval between the collection of the image data and the surgical procedure. To align the images of the fiducials with the fiducial positions in patient space, the tip of the wand is placed on each fiducial or tattooed marker point 164. The coordinates in patient space of each vertebra process tip or fiducial are determined with the procedure described in conjunction with FIGS. 5A–5C.

Figures 6A, 6B:
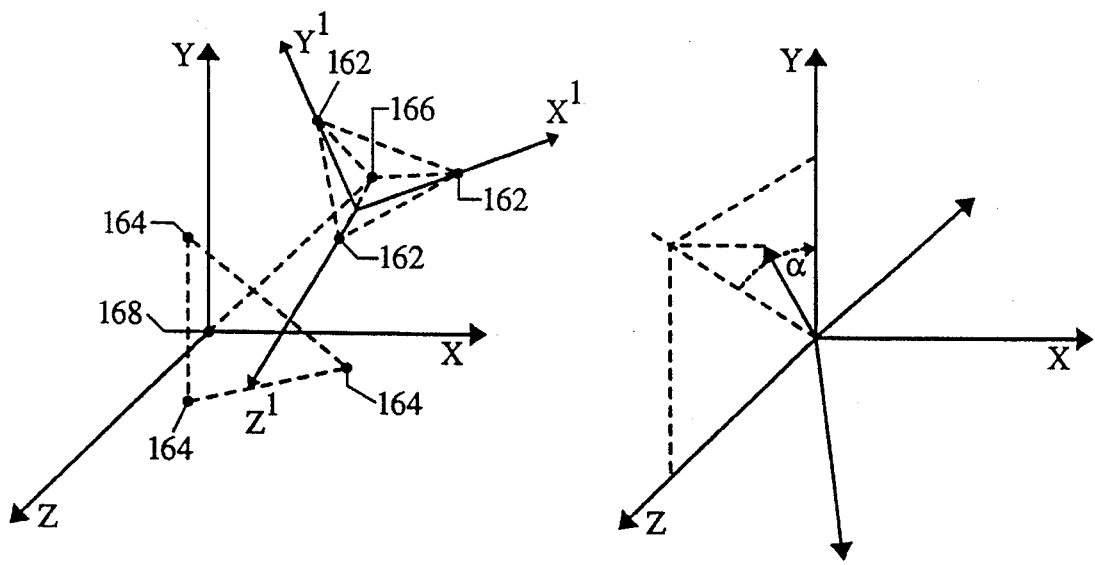
FIGS. 6A, 6B, 6C, and 6D are illustrative of a preferred coordinate transform between the coordinate system of the data and the patient.

The position of the three fiducials or process tips are compared with the relative position of the pixels 162 in the image space. The patient space coordinates of marks 164 or the process tips of the patient in the coordinate system of the patient support are measured. A like coordinate system through the pixels 162 is defined and compared to the patient space coordinate system. The translation and rotational relationship between image space and patient space coordinate systems is determined. With reference to FIG. 6A, the position of the patient in operating room space $(x,y,z)$ and the relative position in image space $(x',y',z')$ are determined. That is, two coordinate systems are defined. The translation means first determines the offset $x_{offset}$, $Y_{offset}$, $z_{offset}$ between the barycenters 166, 168 of the triangles defined by the coordinates of three fiducials or process tips in data and patient space, respectively. This provides a translation or an offset in the x, y, and z-directions between the two coordinate systems. The values of $x_{offset}$, $y_{offset}$, and $z_{offset}$ are added or subtracted to the coordinates of the patient space and the coordinates of image space, respectively, to translate between the two.

Figures 6C, 6D:
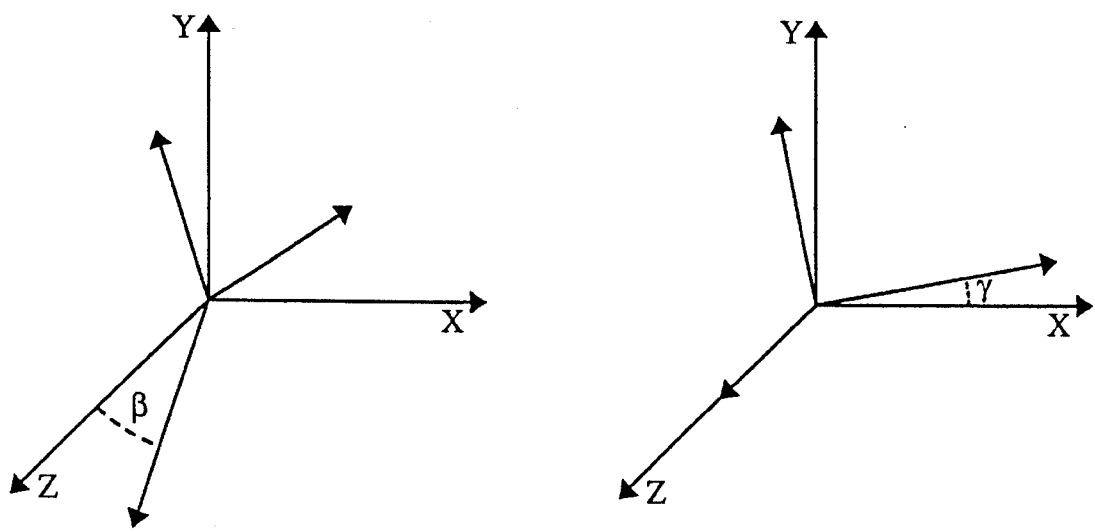

With reference to FIG. 6B, translating the origins of the two coordinate systems into alignment, however, is not the complete correction. Rather, the coordinate systems are normally also rotated relative to each other about all three axes whose origin is at the barycenter. As illustrated in FIGS. 6B, 6C, and 6D, the angle of rotation in the (y,z), (x,z), and (x,y) planes are determined. Having made these determinations, it is a simple matter to transform the patient support space coordinates into the image space coordinates and, conversely, to rotate the image space coordinates into patient space coordinates. The wand coordinate means 130 is connected through the transform 160 with one of the plane selecting means 24 and the video processor 28 to cause a marker, e.g. cross hairs, to be displayed on the monitors 30 at the coordinates of the wand tip. This enables the surgeon to coordinate specific points on the patient or in the incision with the images.

Having aligned the image and patient spaces the wand and tool guide can be used to identify the entry coordinate and trajectory at which the surgical tool will be applied to the patient. For example, the surgeon may use the wand and tool guide in combination to identify the trajectory and coordinate on the spinal column at which the surgeon will utilize a surgical drill in order to drill a hole for the placement of a spinal screw. Holding the wand and drill guide in one hand, the surgeon moves the combination around the exposed vertebra while viewing images displayed on a monitor selected in accordance with the wand tip. The image provide a cross-sectional view of the vertebra and allow the surgeon to plan with greater accuracy the angle and depth at which the drill will be operated. Once the coordinate and trajectory of the drill application is identified, the surgeon may remove the wand while holding the tool guide in place. Since the tool guide comes with a handle, the surgeon can hold the tool guide in place even when the spinal column moves in response to patient breathing. In other words, the surgeon can easily hold the bore of the tool guide at the trajectory identified even while the spinal column experiences movement. With the guide properly oriented, the surgeon inserts into the bore the surgical tool and tip needed for the spinal screw fixation. This technique is superior over prior methods in which surgeons relied solely on their own skill and knowledge of the patient's unique anatomy and will result in far fewer sub-optimal results.

The present invention is also useful in preplanning a surgical operation. For example, surgeons may use images of the body portion at which the surgical tool will be inserted in order to determine prior to the operation, the best trajectory and coordinate at which the tool should be applied. Once the proper trajection and coordinate are identified, the computer system can store these images in memory to be later used as a reference target to be compared with images produced in connection with the wand and drill guide. In particular, the images produced in accordance with the wand and drill guide could be compared with the stored images until the computer identifies an image match. Once the computer identifies a match, the computer can output a signal to alert the surgeon that the tool guide has been properly oriented.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A system for designating a coordinate and trajectory on a subject and for guiding a tool at the coordinate and along the trajectory as the tool is applied to the subject, the system comprising:

a subject support;

a means for securing a preselected portion of the subject to the subject support;

a frame assembly which mounts at least three receivers in a fixed relationship to the subject support;

a wand having a tip portion, a portion extending along a pointing axis of the wand, an offset portion which is offset from the pointing axis of the wand, and at least two wand emitters being mounted in a spaced relationship to the offset portion in a fixed relationship to the pointing axis of the wand, the emitters selectively emitting wand signals which are received by the at least three receivers;

a guide defining a path extending longitudinally along a guide axis, the path being configured for selectively receiving a tool and the tip portion;

a wand position determining means for determining a position of the wand tip portion by measuring wand signal travel of the wand signals between the wand emitters and the at least three receivers.

2. The system of claim 1 further including:

a three-dimensional image memory for storing image data indicative of a three-dimensional region of the portion of the subject which is secured to the subject support;

a plane selecting means for selecting planar slices of data from the three-dimensional image memory;

a display for converting the selected slices of data from the plane selecting means into human-readable displays;

a transform means for transforming a position of the wand tip portion into a coordinate system of the image data stored in the three-dimensional image memory, the transform means being operatively connected with the plane selecting means such that the displayed images have a preselected relationship to a position of the wand.

3. The system of claim 2 wherein the frame assembly is mounted directly to the subject support to be movable therewith such that movement of the subject support does not alter the subject coordinate system.

4. The system of claim 2 further including:

at least three markers disposed at selected subject portions when the three-dimensional image data was acquired such that locations of the three markers are identifiable in the three-dimensional image data; and a transform calculating means for calculating a transform between (1) positions of the markers on the subject denoted by selectively placing the wand tip on each of the markers and (2) the marker locations in the three-dimensional image data, whereby translational and rotational relationships are calculated between subject space coordinate system and a three-dimensional image data space coordinate system.

5. The system of claim 4 wherein the markers contain materials which are visible in both magnetic resonance and CT imaging techniques such that the same markers can be used for both CT and magnetic resonance examinations.

6. An apparatus for orienting a tool and guiding an application of the tool to a subject comprising:

a wand for designating at least a pointing axis, said wand having at least two signal emitters mounted thereto for emitting signals;

at least three receivers mounted in a fixed relationship for receiving the signals emitted by the wand emitters;

a wand position determining means for determining a position of the pointing axis by measuring travel of the signals between the wand emitters and the receivers; and a guide for guiding a tool along a guide axis, said guide having a means for selectively receiving each of the tool and the wand individually and constraining the received wand.

7. The apparatus of claim 6 wherein the wand includes a tip end, a portion extending along the pointing axis of the wand, and an offset portion which is offset from the pointing axis, the wand emitters being mounted in a spaced relationship to the offset portion in alignment with the pointing axis of the wand.

8. The apparatus of claim 6 further including a plurality of tips and a connecting means for selectively connecting each of the tips to the wand.

9. The apparatus of claim 6 wherein the guide includes a tubular member defining a bore therethrough along the guide axis, the bore being configured to receive the tool and the wand.

10. The apparatus of claim 6 wherein the guide includes a grooved portion defining a groove extending therethrough along the guide axis, the groove being configured to receive the tool.

11. The apparatus of claim 10 wherein the guide includes a securing means connected to the grooved portion, for selectively (1) securing the tool to the grooved portion and (2) securing the wand in the grooved member with the pointing axis and the guide axis in alignment.

12. The apparatus of claim 6 wherein the guide and the wand are integrally connected.

13. The apparatus of claim 6 wherein the wand includes a tip portion, a portion extending along the pointing axis of the wand, and an offset portion which is offset from the pointing axis, the wand emitters being mounted in a spaced relationship to the offset portion in alignment with the pointing axis of the wand, said guide being configured to receive the wand portion which extends along the pointing axis such that the pointing and guide axes are coincident.

14. The apparatus of claim 13 wherein the wand includes a wand stop fixedly connected to the wand portion which extends along the pointing axis, the wand stop abutting a guide stop surface when the guide receives the wand.

15. The apparatus of claim 13 wherein the wand includes a laser mounted to the offset portion, an output light of the laser being projected along the guide axis.

16. An apparatus for guiding an application of a tool to a subject from an entry point along a trajectory, the apparatus comprising:

- a guide member defining a guide axis and having a terminal end positionable on a selected subject entry point, said guide member being configured to support a tool along the guide axis;
- a handle connected to the guide member, for holding the terminal end at the selected entry point and for holding the guide axis steady;
- a means for emitting signals indicative of an orientation of the guide axis;
- a receiver for receiving the emitted signals;
- a means connected with the receiver for determining the orientation of the guide axis from the signals;
- a means for storing a diagnostic image of the subject;
- a means for correlating the guide axis with a coordinate system of the diagnostic data;
- a display means for displaying a selected portion of the diagnostic data with the guide axis superimposed thereon.

17. The apparatus of claim 16 wherein the guide member defines a bore in alignment with the guide axis.

18. The apparatus of claim 16 wherein the guide member defines a groove extending in alignment with the guide axis.

19. The apparatus of claim 16 wherein the signal emitting means includes:

- a wand which is configured for receipt in the guide member;
- at least two emitters affixed to the wand, in a preselected relationship to the guide axis.

20. The apparatus of claim 19 further including a connecting means for releasibly interconnecting the wand and the guide member.

21. The apparatus of claim 19 further including a plurality of wand tips and a connecting means for selectively connecting each of the wand tips to the wand.

22. A method of orienting a tool and guiding an application of the tool to a subject, the method comprising:

a) maneuvering a wand and guide in combination to a proposed entry point and trajectory for application of the tool, the wand including signal emitters;

b) calculating coordinates of the signal emitters from travel times between signals emitted from the emitters and received by at least three receivers held in fixed relationship to the subject;

c) calculating a trajectory and entry point from the emitter coordinates;

d) correlating the calculated entry point and trajectory with electronic diagnostic image data of the subject stored in computer memory;

e) generating a human-readable display of at least a portion of the image data with the trajectory and entry point superimposed thereon;

f) inserting the tool into the guide while maintaining the guide steady at the proposed entry point;

g) applying the tool to the subject through the guide along the proposed trajectory to the proposed entry point.

23. The method of claim 22 further comprising:

inserting a pointing portion of the wand into the guide prior to the maneuvering step, the wand carrying the emitters; and removing the pointing portion of the wand from the guide prior to the step of inserting the tool into the guide.

* * * * *